(12) United States Patent
Tsai et al.

(10) Patent No.: US 12,012,589 B2
(45) Date of Patent: Jun. 18, 2024

(54) *LACTOBACILLUS* COMPOSITION AND USE THEREOF FOR IMPROVING ANXIETY CAUSED BY ANTIBIOTICS

(71) Applicant: GenMont Biotech Incorporation, Tainan (TW)

(72) Inventors: Wan-Hua Tsai, Tainan (TW); Wen-Ling Yeh, Tainan (TW); Chia-Lin Wu, Tainan (TW); Chih-Ho Lai, Tainan (TW); Yao-Tsung Yeh, Tainan (TW); Cheng-Hsieh Huang, Tainan (TW)

(73) Assignee: GENMONT BIOTECH INCORPORATION, Tainan (TW)

( * ) Notice: Subject to any disclaimer, the term of this patent is extended or adjusted under 35 U.S.C. 154(b) by 0 days.

(21) Appl. No.: 17/561,030

(22) Filed: Dec. 23, 2021

(65) Prior Publication Data
US 2023/0081322 A1 Mar. 16, 2023

(30) Foreign Application Priority Data
Sep. 6, 2021 (TW) .................. 110133093

(51) Int. Cl.
*C12N 1/20* (2006.01)
*A61K 35/00* (2006.01)
(Continued)

(52) U.S. Cl.
CPC .............. *C12N 1/205* (2021.05); *A61K 35/00* (2013.01); *A61P 25/22* (2018.01);
(Continued)

(58) Field of Classification Search
CPC .. C12N 1/205; A61K 35/00; A61K 2035/115; A61P 25/22; C12R 2001/225; C12R 2001/23; C12R 2001/25
See application file for complete search history.

(56) References Cited

U.S. PATENT DOCUMENTS

2017/0312232 A1* 11/2017 Vitetta .................. A23L 33/135

FOREIGN PATENT DOCUMENTS

| CN | 111728111 A | * | 10/2020 | ............... A23L 2/52 |
| WO | WO-2016065419 A1 | * | 5/2016 | ............... A23L 2/52 |

OTHER PUBLICATIONS

Bravo et al. Ingestion of Lactobacillus strain regulates emotional behavior and central GABA receptor expression in a mouse via the vagus nerve. Proc Natl Acad Sci U S A. Sep. 20, 2011;108(38) (Year: 2011).*

(Continued)

*Primary Examiner* — Thomas J. Visone
(74) *Attorney, Agent, or Firm* — WPAT, P.C

(57) ABSTRACT

The present invention provides a *Lactobacillus* composition and a use thereof for improving anxiety caused by antibiotics, wherein the *Lactobacillus* composition comprises *Lactobacillus plantarum* GMNL-141, *Lactobacillus rhamnosus* GM-020, *Lactobacillus acidophilus* GMNL-185, or a combination thereof. The *Lactobacillus* composition can effectively improve imbalance of an individual's intestinal flora caused by antibiotics to help stabilize and increase species richness and increase the synthesis of mood-stabilizing compounds, including flavonoids, flavonols, isoquinoline alkaloids, niacinamide, nicotinamide, and short-chain fatty acids in intestine, and thus effectively improve antibiotic-induced with anxiety disorders.

6 Claims, 8 Drawing Sheets
Specification includes a Sequence Listing.

(51) Int. Cl.
*A61P 25/22* (2006.01)
*C12R 1/225* (2006.01)
*C12R 1/23* (2006.01)
*C12R 1/25* (2006.01)

(52) U.S. Cl.
CPC ... *A61K 2035/115* (2013.01); *C12R 2001/225* (2021.05); *C12R 2001/23* (2021.05); *C12R 2001/25* (2021.05)

(56) References Cited

OTHER PUBLICATIONS

Jang HM, Lee HJ, Jang SE, Han MJ, Kim DH. Evidence for interplay among antibacterial-induced gut microbiota disturbance, neuro-inflammation, and anxiety in mice. Mucosal Immunol. Sep. 2018;11(5):1386-1397. (Year: 2018).*

Rudzki L, et al. Probiotic Lactobacillus Plantarum 299v decreases kynurenine concentration and improves cognitive functions in patients with major depression: A double-blind, randomized, placebo controlled study. Psychoneuroendocrinology. 2019. (Year: 2019).*

Markowiak-Kopeć P, Śliżewska K. The Effect of Probiotics on the Production of Short-Chain Fatty Acids by Human Intestinal Microbiome. Nutrients. 2020; 12(4):1107. (Year: 2020).*

Arslanova et al., Life, 11(764):1-20 (2021) (Year: 2021).*

Ceylani et al., Heliyon 4:e00644 (2018) (Year: 2018).*

Mirsa et al., Crit. Rev. Food Sci. Nutr., 59(8):1230-1236 (2019) (Year: 2019).*

Park et al., Nutrients, 13(811):1-10 (2021) (Year: 2021).*

* cited by examiner

LACTOBACILLUS COMPOSITION AND USE THEREOF FOR IMPROVING ANXIETY CAUSED BY ANTIBIOTICS

CROSS-REFERENCE TO RELATED APPLICATION

This application claims priority of Taiwan application No. 110133093, filed on Sep. 6, 2021, the content of which are incorporated herein in its entirety by reference.

STATEMENT REGARDING SEQUENCE LISTING

The sequence listing associated with this application is provided in text format in lieu of a paper copy and is hereby incorporated by reference into the specification. The name of the txt file containing the sequence listing is sl. The txt file is 1,441 bytes; was created on Dec. 23, 2021.

BACKGROUND OF THE INVENTION

1. Field of the Invention

The present invention relates to a *Lactobacillus* composition and use thereof for improving anxiety caused by antibiotics, and more particularly to a *Lactobacillus* composition comprising *Lactobacillus plantarum* GMNL-141, *Lactobacillus rhamnosus* GM-020, *Lactobacillus acidophilus* GMNL-185, or a combination thereof, and use thereof for improving anxiety caused by antibiotics.

2. The Prior Art

Anxiety disorders are the most common mental illnesses, with about one in eight people in the world suffering from the disorder. The main symptom of anxiety disorder is excessive anxiety and worry, which will cause autonomic nerve hyperactivity, chest tightness, palpitations, night sweats, gastrointestinal discomfort, and may be accompanied by symptoms such as restlessness, irritability, fatigue, muscle tightness, insomnia, lack of concentration, or a blank brain, which affects the normal life of patients.

Antibiotics are chemicals that can inhibit the growth of bacteria or kill the bacteria, and are the most commonly used clinical drugs to treat and prevent bacterial infection-related diseases. However, many recent studies have pointed out that the use of antibiotics may disturb the composition of the gut microbiota of patients, which in turn may trigger the side effects of neuropsychiatric diseases such as schizophrenia, autism, anxiety, and depression.

Previous studies have been found that individual's gut microbiota and metabolites thereof are related to maintaining the balance of the individual's nervous, endocrine, and immune systems. Under the stimulation of stressors, the hypothalamus-pituitary-adrenal axis secretes glucocorticoids, epinephrine, and norepinephrine, which may increase the expression and secretion of pro-inflammatory cytokines in immune cells, thereby disturbing the composition of intestinal flora of the individual, and may therefore lead to anxiety or other neuropsychiatric related diseases.

At present, the exact relationship between different diseases and different intestinal flora has not been fully characterized, and it has not yet been known which specific flora is additionally administered, which can have a definite effect on the intestinal and systemic levels and on any specific type of disease, especially for diseases of the central nervous system.

In summary, in the art related to probiotics, it is necessary to find new methods to effectively treat specific diseases, especially the side effects such as anxiety caused by the high frequency of antibiotics.

SUMMARY OF THE INVENTION

To solve the foregoing problem, one objective of the present invention is to provide a *Lactobacillus plantarum* strain GMNL-141 which is deposited at National Institute of Technology and Evaluation (NITE) with an accession number NITE BP-03510, wherein the *Lactobacillus plantarum* strain GMNL-141 is in a lyophilized or spray dried form.

The further objective of the present invention is to provide a *Lactobacillus* composition comprising a *Lactobacillus plantarum* GMNL-141 which is deposited at NITE with an accession number NITE BP-03510.

In one embodiment of the present invention, the *Lactobacillus* composition further comprises a *Lactobacillus rhamnosus* GM-020 which is deposited at China Type Culture Collection (CCTCC) with an accession number CCTCC M203098, a *Lactobacillus acidophilus* GMNL-185 which is deposited at CCTCC with an accession number CCTCC M2017764, or a combination thereof.

In one embodiment of the present invention, the *Lactobacillus plantarum* GMNL-141, the *Lactobacillus rhamnosus* GM-020, and the *Lactobacillus acidophilus* GMNL-185 are alive or dead bacteria.

In one embodiment of the present invention, the *Lactobacillus plantarum* GMNL-141, the *Lactobacillus rhamnosus* GM-020, and the *Lactobacillus acidophilus* GMNL-185 are mixed with a ratio of 1:1:1.

In one embodiment of the present invention, the *Lactobacillus* composition is a medicine, a nutritional supplement, a health food, or any combination thereof.

In one embodiment of the present invention, the *Lactobacillus* composition further comprises a pharmaceutically acceptable excipient, carrier, adjuvant, and/or food additive.

In one embodiment of the present invention, the *Lactobacillus* composition is in the form of a solution, a suspension, a semi-solid preparation, a solid preparation, a gelatin capsule, a soft capsule, a tablet, a pill, a syrup, a lozenge, a troche, a chewing gum, and/or a freeze-dried powder preparation.

The other objective of the present invention is to provide a method of improving anxiety caused by an antibiotic, comprising administering to a subject in need thereof a *Lactobacillus* composition comprising a *Lactobacillus plantarum* GMNL-141 which is deposited at NITE with an accession number NITE BP-03510.

In one embodiment of the present invention, the antibiotic is Ampicillin.

In one embodiment of the present invention, the *Lactobacillus* composition further comprises a *Lactobacillus rhamnosus* GM-020 which is deposited at China Type Culture Collection (CCTCC) with an accession number CCTCC M203098, a *Lactobacillus acidophilus* GMNL-185 which is deposited at CCTCC with an accession number CCTCC M2017764, or a combination thereof.

In one embodiment of the present invention, the *Lactobacillus* composition improves imbalance of intestinal flora and/or decrease in intestinal flora species richness caused by the antibiotic.

In one embodiment of the present invention, the *Lactobacillus* composition increases the abundance of *Bifidobacterium* and/or decreases the abundance of *Staphylococcus* in intestinal flora.

In one embodiment of the present invention, the *Lactobacillus* composition increases the synthesis of flavone and flavonol, the synthesis of isoquinoline alkaloid, and/or the synthesis of nicotinate and nicotinamide.

In one embodiment of the present invention, the *Lactobacillus* composition increases the synthesis of short-chain fatty acids (SCFAs) in intestine.

In one embodiment of the present invention, an effective amount of the *Lactobacillus* composition is at least $6.7 \times 10^8$ cfu/kg per day.

According to the present invention, the *Lactobacillus rhamnosus* GM-020, the *Lactobacillus plantarum* GMNL-141, and the *Lactobacillus acidophilus* GMNL-185 that provide the best efficacy in improving anxiety caused by antibiotics are screened out by animal experiments, and these three probiotic bacteria are prepared into the probiotic composition of the present invention in a compound formula. Moreover, no matter the low-dose or high-dose probiotic composition of the present invention is proved to effectively improve the anxious behavior of individuals caused by antibiotics, and the efficacy thereof is better than that of a single probiotic bacteria.

Furthermore, the probiotic composition of the present invention can improve the imbalance of individual intestinal flora caused by antibiotics, and assist in stabilizing and increasing the intestinal flora species richness, especially increasing the abundance of *Bifidobacterium* and decreasing the abundance of *Staphylococcus*, so that the individual intestinal flora can quickly return to a state close to that of a healthy individual. In addition, the probiotic composition of the present invention can increase the biosynthesis of flavonoids and flavonols, the biosynthesis of isoquinoline alkaloids, and nicotinate, and the metabolism of nicotinate and nicotinamide by adjusting the intestinal flora of individuals, and can also directly increase the synthesis of short-chain fatty acids in intestine, thereby improving individual anxiety or anxious behavior caused by antibiotics.

The embodiments of the present invention are further described with the following drawings. The following embodiments are given to illustrate the present invention and are not intended to limit the scope of the present invention, and one with ordinary skill in the art can make some modifications and refinements without departing from the spirit and scope of the present invention. Therefore, the scope of the present invention is defined by the scope of the appended claims.

Figure 1A:
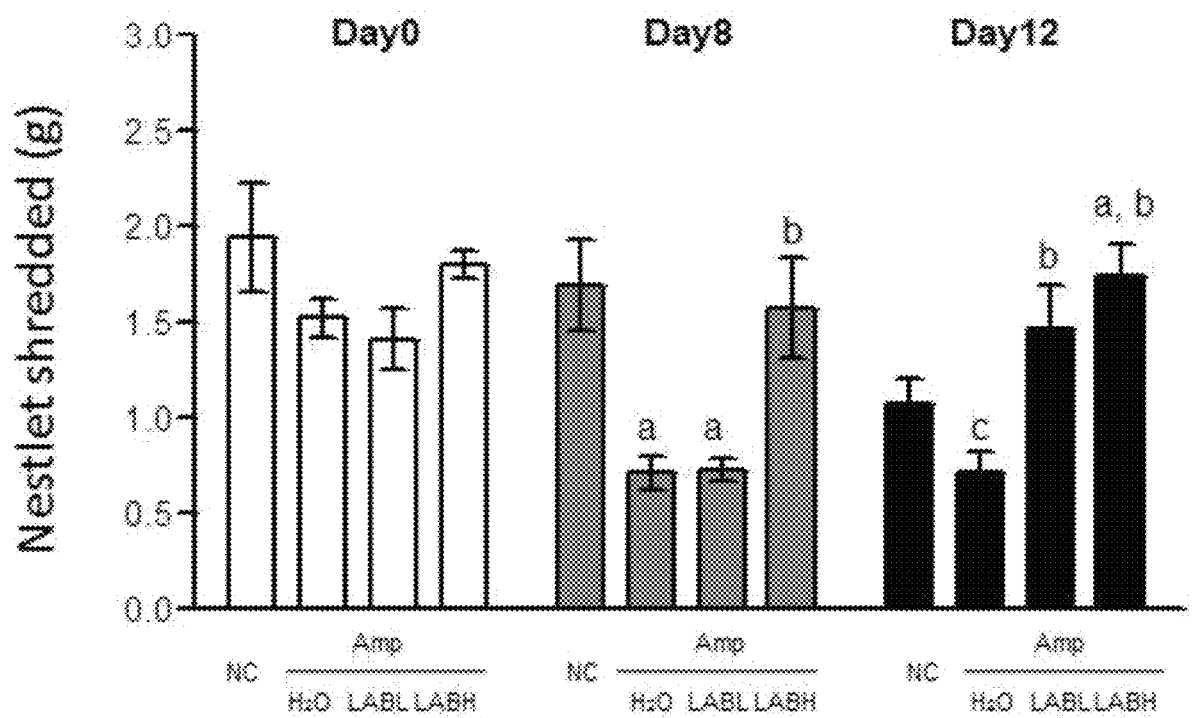
FIG. 1A shows the results of improving nesting capacity of mice after being fed with the probiotic composition of the present invention; wherein, a represents compared with NC, P<0.05; b represents compared with Amp $H_2O$, P<0.05; and c represents compared with NC, P=0.06.

In the above FIGs., NC represents mice that have not been pre-treated with antibiotics to have anxiety and were not fed with the probiotic composition of the present invention; Amp or Amp $H_2O$ represents mice that have been pre-treated with antibiotics to have anxiety but were not further fed with the probiotic composition of the present invention; Amp LABL or Amp-LABL represents mice that have been pre-treated with antibiotics to have anxiety and then were further fed with a low-dose of the probiotic composition of the present invention; Amp LABH or Amp-LABH represents mice that have been pre-treated with antibiotics to have anxiety and then were further fed with a high-dose of the probiotic composition of the present invention.

DETAILED DESCRIPTION OF THE PREFERRED EMBODIMENT

All technical and scientific terms used herein, unless otherwise defined, have the meaning commonly understood by one with ordinary skill in the art.

The term "effective amount" described herein refers to the amount of the probiotic composition required to effectively improve anxiety or anxious behavior in mammals or humans caused by antibiotics; the amount of the probiotic composition required to effectively improve imbalance of intestinal flora and/or decrease in intestinal flora species richness in mammals or humans caused by antibiotics; the amount of the probiotic composition required to effectively increase the abundance of *Bifidobacterium* and/or decrease the abundance of *Staphylococcus* in intestinal flora; the amount of the probiotic composition required effectively increase the synthesis of flavone and flavonol, the synthesis of isoquinoline alkaloid, and/or the synthesis of nicotinate and nicotinamide in intestine of mammals or humans; the amount of probiotic composition required to effectively increase the synthesis of short chain fatty acids in intestine of mammals or humans. The effective amount may vary depending on the type of organism or the individual administered, but may be determined experimentally by, for example, a dose escalation test.

The term "probiotic composition" described herein refers to a *Lactobacillus* composition comprising a *Lactobacillus plantarum* GMNL-141, or the *Lactobacillus* composition further comprising a *Lactobacillus rhamnosus* GM-020 and/or a *Lactobacillus acidophilus* GMNL-185.

The data provides in the present invention represent approximated, experimental values that vary within a range of ±20%, preferably ±10%, and most preferably ±5%.

Statistical analysis was performed using Excel software. Data were expressed as mean±standard error (SEM), and Student's t-test was used to analyze whether the sample mean between two groups is statistically significant (P<0.05).

The term "probiotic or probiotic bacteria" described herein refers to a microorganism and the cells, the mixed strains, the extracts or the metabolites thereof with a positive effect on the host itself, usually derived from individual's body and beneficial to health of the individual, and may also be certain microorganisms that are externally supplemented and be beneficial to the individual.

According to the present invention, the operating procedures and parameter conditions for bacterial culture are within the professional literacy and routine techniques of one with ordinary skill in the art.

According to the present invention, the operating procedures and parameter conditions for tube feeding of bacterial composition (or probiotic composition described herein) to experimental animals are within the professional literacy and routine techniques of one with ordinary skill in the art.

According to the present invention, the operating procedures and parameter conditions for detection and analysis of intestinal flora in experimental animals are within the professional literacy and routine techniques of one with ordinary skill in the art.

The term "richness" described herein refers to the diversity of species, e.g., species richness indicates the diversity of species, while the term "abundance" described herein refers to the abundance of a single species, e.g., bacterial abundance indicates the abundance of the bacterium.

The present invention provides a novel *Lactobacillus plantarum* (*L. plantarum*) strain GMNL-141, which is a probiotic bacteria strain with the ability to improve anxiety or anxious behaviors caused by antibiotics; the *Lactobacillus plantarum* GMNL-141 of the present invention was isolated from intestinal specimens of human small intestine. After the total RNA of the *Lactobacillus plantarum* GMNL-141 was extracted by conventional methods, the sequence of the 16S rRNA gene was amplified by primer pairs as shown in SEQ ID NO: 1 and SEQ ID NO: 2 (PAF primer as the upstream primer and 536R primer as the downstream primer), and the resulting nucleic acid sequence was shown as SEQ ID NO: 3; wherein, methods of extracting the total RNA is well known to one with ordinary skill in the art and thus the details are not described herein. Next, the nucleic acid sequence (SEQ ID NO: 3) was then compared with the 16S rRNA gene sequences of seven *Lactobacillus plantarum* strains from GenBank of the National Center for Biotechnology Information, NCBI, (NR_117813.1, NR_104573.1, NR_042394.1, NR_029133.1, NR_113338.1, NR_115605.1, and NR_136785.1, respectively) and the result showed more than 99% sequence identity, so the GMNL-141 strain was confirmed as *Lactobacillus plantarum* (*L. plantarum*).

The PAF primer:
(SEQ ID NO: 1)
5'-AGAGTTTGATCCTGGCTCAG-3'.

The 536R primer:
(SEQ ID NO: 2)
5'-GTATTACCGCGGCTGCTG-3'.

The sequence of the 16S rRNA gene of the *Lactobacillus plantarum* GMNL-141:

(SEQ ID NO: 3)
GGCGTGCGGCGTGCTATACATGCAAGTCGAACGAAC

TCTGGTATTGATTGGTGCTTGCATCATGATTTACA

TTTGAGTGAGTGGCGAACTGGTGAGTAACACGTGG

GAAACCTGCCCAGAAGCGGGGGATAACACCTGGAA

ACAGATGCTAATACCGCATAACAACTTGGACCGCA

TGGTCCGAGTTTGAAAGATGGCTTCGGCTATCACT

TTTGGATGGTCCCGCGGCGTATTAGCTAGATGGTG

GGGTAACGGCTCACCATGGCAATGATACGTAGCCG

ACCTGAGAGGGTAATCGGCCACATTGGGACTGAGA

CACGGCCCAAACTCCTACGGGAGGCAGCAGTAGGG

AATCTTCCACAATGGACGAAAGTCTGATGGAGCAA

CGCCGCGTGAGTGAAGAAGGGTTTCGGCTCGTAAA

ACTCTGTTGTTAAAGAAGAACATATCTGAGAGTAA

CTGTTCAGGTATTGACGGTATTTAACCAGAAAGCC

ACGGCTAACTACGTGCCAGCAGCCGGGGTAATACA

A.

The physiological characteristics of the *Lactobacillus plantarum* GMNL-141 of the present invention are as follows: the growth temperature is 35° C. to 40° C., the growth acid-base value is pH 4.0 to 7.0, and the influence of oxygen is facultative anaerobic; the method for culturing the *Lactobacillus plantarum* GMNL-141 of the present invention is as follows: the GMNL-141 strain is cultured with agar medium (De Man, Rogosa and Sharpe, MRS) at 37°C; the appearance characteristics of the colony of the *Lactobacillus plantarum* GMNL-141 of the present invention are as follows: the edge is complete, the average size is 3 mm×3 mm, the colony is slightly white and large, and the surface is smooth and raised; the morphological characteristics of the *Lactobacillus plantarum* GMNL-141 of the present invention are as follows: rod-shaped (bacilli), no sporulation, and no mobility; and the Gram staining result of the *Lactobacillus plantarum* GMNL-141 of the present invention is positive.

The *Lactobacillus plantarum* GMNL-141 of the present invention has been deposited at Biological Resource Center of National Institute of Technology and Evaluation (NITE) on Aug. 23, 2021, and the accession number is NITE BP-03510.

Compared with the commercial strain of *Lactobacillus plantarum* CCTCC M2017767, when the *Lactobacillus plantarum* GMNL-141 of the present invention is fed to mice with anxiety induced by antibiotics, the effect of *Lactobacillus plantarum* GMNL-141 on improving anxiety in mice is obviously better than that of the commercial strains of same species.

Based on the beneficial biological activity described above, the *Lactobacillus plantarum* GMNL-141 of the present invention is expected to have the potential to be used to improve anxiety-related disorders. Therefore, the present invention also provides a *Lactobacillus* composition comprising the *Lactobacillus plantarum* GMNL-141 of the present invention, which may further comprise: a *Lactobacillus rhamnosus* (*L. rhamnosus*) GM-020, a *Lactobacillus acidophilus* (*L. acidophilus*) GMNL-185, or a combination thereof; wherein, the *Lactobacillus rhamnosus* GM-020 and the *Lactobacillus acidophilus* GMNL-185 have been deposited in China Type Culture Collection (CCTCC). The accession number of the *Lactobacillus rhamnosus* GM-020 is CCTCC M203098, and the deposit date is Dec. 18, 2003. The accession number of the *Lactobacillus acidophilus* GMNL-185 is CCTCC M2017764, and the deposit date is Nov. 3, 2017. The *Lactobacillus plantarum* GMNL-141, the *Lactobacillus rhamnosus* GM-020, and the *Lactobacillus acidophilus* GMNL-185 also include subculture generations thereof or mutant strains thereof, but still have the same characteristics, genome, or use as the strains described herein. The *Lactobacillus plantarum* strain GMNL-141, the *Lactobacillus rhamnosus* GM-020, and the *Lactobacillus acidophilus* GMNL-185 will be publicly available upon the granting of the present application.

The *Lactobacillus* composition of the present invention can be applied to a preparation of a pharmaceutical composition for improving anxiety caused by antibiotics; wherein, the pharmaceutical composition may be a medicine, a nutritional supplement, a health food, or any combination thereof, and may further include a pharmaceutically acceptable excipient, carrier, adjuvant, and/or food additives.

In one preferred embodiment of the present invention, the *Lactobacillus* composition of the present invention is formulated in a pharmaceutically acceptable vehicle, and is made into a suitable dosage form of an oral administration of, and the pharmaceutical composition is preferably in a dosage form selected from the following group: a solution, a suspension, a powder, a tablet, a pill, a syrup, a lozenge, a troche, a chewing gum, a capsule, and the like.

According to the present invention, the pharmaceutically acceptable vehicle may include one or more reagents selected from the following: a solvent, a buffer, an emulsifier, a suspending agent, a decomposer, a disintegrating agent, a dispersing agent, a binding agent, an excipient, a stabilizing agent, a chelating agent, a diluent, a gelling agent, a preservative, a wetting agent, a lubricant, an absorption delaying agent, a liposome, and the like. The selection and quantity of these reagents is a matter of professionalism and routine for one with ordinary skill in the art.

According to the present invention, the pharmaceutically acceptable vehicle may include a solvent selected from the group consisting of: water, normal saline, phosphate buffered saline (PBS), aqueous solution containing alcohol, and combinations thereof.

In another preferred embodiment of the present invention, the *Lactobacillus* composition of the present invention can be prepared into a food product, and be formulated with edible materials which include but not limited to: beverages, fermented foods, bakery products, health foods, nutritional supplements, and dietary supplements.

According to the present invention, the edible material is selected from the group consisting of: water, fluid milk products, milk, concentrated milk, fermented milk, such as yogurt, sour milk, frozen yogurt, lactic acid bacteria-fermented beverages, milk powder, ice cream, cream cheeses, dry cheeses, soybean milk, fermented soybean milk, vegetable-fruit juices, juices, sports drinks, confectionery, jelly, candies, infant formulas, health foods, animal feeds, Chinese herbals, and dietary supplements.

According to the present invention, food products can be used as a food additive, which is added during the preparation of raw materials by conventional methods, or added during the production process of food, and can be formulated with any edible material into food products for human and non-human animals to eat.

The following will describe in detail: the screening method of the probiotic bacteria strains in the probiotic composition of the present invention; the efficacy test of the probiotic composition of the present invention for improving anxiety caused by antibiotics, and the analysis of the specific mechanism of the probiotic composition of the present invention for improving anxious behavior caused by antibiotics, and thus to prove that the probiotic composition of the present invention provides the effect of improving anxiety caused by antibiotics, and can be used to prepare a composition with corresponding effects.

Example 1

Screen of the Probiotic Bacteria Strains in the Probiotic Composition

In the embodiment of the present invention, in order to screen probiotic bacteria strains that can effectively improve anxious behavior of individuals caused by antibiotics, the mice with anxious behavior induced by antibiotics were used as experimental animals for testing, and decrease in swimming survival ability of the mice was used as the indicator of anxiety caused by antibiotics in mice. The detailed test method is as following: first, 7-week-old male mice of the C57BL/6 strain were gotten from the National Laboratory Animal Center of Taiwan, and before the test, the mice were adapted for one week at the environment of following test. Then, in order to avoid differences in mice among each test group, the swimming survival ability of each mouse was evaluated on the day before the test.

Then, the mice were divided into the twelve groups, and the groups (1) to (10) were experimental groups of mice that were fed with probiotic bacteria (Test). In the experimental groups, the mice were given antibiotics orally for two consecutive days (ampicillin was used in the embodiment of the present invention) in order to induce anxiety; wherein, the dose of antibiotics was 100 mg/kg mice/day, and then the mice were fed with low-dose single probiotic bacteria by tube feeding for five consecutive days from the third day. In the embodiment of the present invention, the probiotic bacteria were freeze-dried powder of live bacteria prepared with 100 μL of sterile water, and the low dose of each probiotic bacteria was $1.6 \times 10^8$ cfu/mouse/day. The probiotic bacteria of the groups (1) to (10) were: (1) *Lactobacillus rhamnosus* (*L. rhamnosus*) GM-020, (2) *Lactobacillus reuteri* (*L. reuteri*) CCTCC M207154, (3) *Lactobacillus fermentum* (*L. fermentum*) CCTCC M204055, (4) *Lactobacillus plantarum* (*L. plantarum*) GMNL-141, (5) *Lactobacillus acidophilus* (*L. acidophilus*) GMNL-185, (6) *Lactobacillus casei* (*L. casei*) CCTCC M2013197, (7) *Lactobacillus fermentum* (*L. fermentum*) CCTCC M2016225, (8) *Lactobacillus paracasei* (*L. paracasei*) CCTCC M2016225, (9) *Lactobacillus rhamnosus* (*L. rhamnosus*) CCTCC M2017766, and (10) *Lactobacillus plantarum* (*L. plantarum*) CCTCC M2017767. The group (11) was a negative control group (Sham): mice were given phosphate buffered saline (PBS solution) orally for two consecutive days, and then sterile Milli-Q ultrapure water (hereinafter referred to as MQ water, Merck) was given for five consecutive days starting from the next day; n=6. The group (12) was a positive control group (Control): mice were given antibiotics orally for two consecutive days (Ampicillin was used in the embodiment of the present invention) in order to induce anxiety; wherein, the dose of antibiotics was 100 mg/kg mice/day, and then sterile MQ water was given for five consecutive days starting from the next day; n=6.

Then, on the fourth day after the mice were fed with probiotic bacteria or MQ water (i.e. the twelfth day of the overall test), the swimming survival ability of each mouse was evaluated. In order to compare and evaluate the efficacy of probiotic bacteria for improving anxious behavior within different individuals, the following formulas (I) was used to quantify the efficacy of the swimming survival ability of the mice after being fed with the probiotic bacteria of groups (1) to (10) respectively, as a reference for selecting the best bacteria:

$$\frac{\text{Value of the difference in time struggling in the water(Test - sham)}}{\text{Value of the difference in time struggling in the water(Control - sham)}} \times 100\%. \quad (I)$$

After the mice with anxiety induced by antibiotics were fed with these ten different probiotic bacteria, the test results of the efficacy of improving the swimming survival ability of the mice were shown in Table 1. As shown in Table 1, the top three with the best efficacy of improving the swimming survival ability of the mice were the *Lactobacillus rhamnosus* GM-020 of the group (1), the *Lactobacillus plantarum* GMNL-141 of the group (4), and the *Lactobacillus acidophilus* GMNL-185 of the group (5), and the efficacy of these three strains was significantly better than other strains of the same species. The results indicated that the *Lactobacillus rhamnosus* GM-020, the *Lactobacillus plantarum* GMNL-141, and the *Lactobacillus acidophilus* GMNL-185 provide the effect of improving anxious behavior. Further, these three probiotic bacteria with the best efficacy were mixed with a ratio of 1:1:1 to form a probiotic composition of the present invention in a composite formula, and the efficacy of the probiotic composition for improving anxious behavior of individuals caused by antibiotics was tested by the above method, and the detailed test method will be described later.

TABLE 1

| Group | Bacterial species | Bacterial strains | n | Recovery rate (%, Mean ± SEM) |
|---|---|---|---|---|
| 1 | L. rhamnosus | GM-020 | 10 | 107.4 ± 25.9 |
| 2 | L. reuteri | CCTCC M207154 | 4 | 45.2 ± 27.4 |
| 3 | L. fermentum | CCTCC M204055 | 10 | 77.4 ± 19.4 |
| 4 | L. plantarum | GMNL-141 | 10 | 156.2 ± 46.7 |
| 5 | L. acidophilus | GMNL-185 | 6 | 132.1 ± 54.0 |
| 6 | L. casei | CCTCC M2013197 | 12 | 69.4 ± 14.0 |
| 7 | L. fermentum | CCTCC M2016225 | 6 | 5.4 ± 22.1 |
| 8 | L. paracasei | CCTCC M2016226 | 6 | 39.2 ± 15.3 |
| 9 | L. rhamnosus | CCTCC M2017766 | 12 | 44.6 ± 14.0 |
| 10 | L. plantarum | CCTCC M2017767 | 6 | 10.8 ± 38.8 |

Example 2

The Probiotic Composition Improves Anxiety Caused by Antibiotics

In the embodiment of the present invention, in order to test the efficacy of the probiotic composition of the present invention described in Example 1 for improving anxious behavior of individuals caused by antibiotics, the method of Example 1 was used, and the mice with anxious behavior induced by antibiotics were used as experimental animals for testing, and decrease in nesting capacity and swimming survival ability of the mice was used as the indicator of anxiety caused by antibiotics in mice.

The detailed test method was as following: first, the nesting capacity and the swimming survival ability of each mouse was evaluated on the day before the test, and then the mice were divided into the group (13) low-dose experimental group (Amp-LABL) and (14) high-dose experimental group (Amp-LABH); n=5, respectively. The mice were given antibiotics orally for two consecutive days in order to induce anxiety; wherein, the dose of antibiotics was 100 mg/kg mice/day, and then the mice were fed with the low-dose or high-dose probiotic composition of the present invention by tube feeding for five consecutive days from the third day; wherein, low dose of the probiotic composition was $1.6 \times 10^8$ cfu/mouse/day, which was equivalent to a 60 kg human adult with dose of $4 \times 10^{10}$ cfu per day; and high dose of the probiotic composition was $4.8 \times 10^8$ cfu/mouse/day, which was equivalent to a 60 kg human adult with dose of $1.2 \times 10^{11}$ cfu per day. In addition, the negative control group (NC) and the positive control group (Amp or Amp H$_2$O) were tested in the same method used in Example 1. The probiotic composition of the present invention of a composite formula was a combination of the *Lactobacillus rhamnosus* GM-020, the *Lactobacillus plantarum* GMNL-141, and the *Lactobacillus acidophilus* GMNL-185 mixed with equal bacterial counts into a high bacterial count powder ($1 \times 10^{11}$ cfu/g), and then the high bacterial count powder was diluted with sterile water to a specific concentration and then fed to the mice.

Figure 1B:
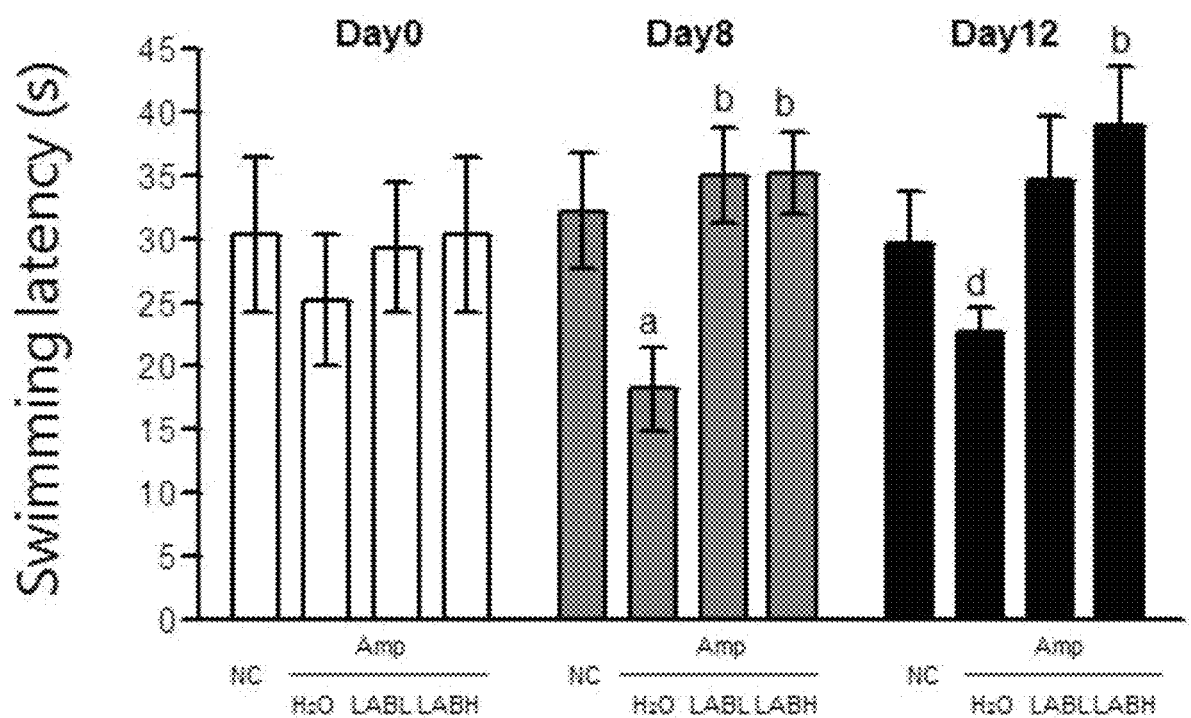
FIG. 1B shows the results of improving swimming survival ability of mice after being fed with the probiotic composition of the present invention; wherein, a represents compared with NC, P<0.05; b represents compared with Amp $H_2O$, P<0.05; and d represents compared with NC, P=0.08.

Then, on the eighth day of the overall test (i.e. the next day after the mice were fed with probiotic bacteria or MQ water), and on the twelfth day of the overall test (i.e. the fourth day after the mice were fed with probiotic bacteria or MQ water), the nesting capability and the swimming survival ability of each mouse was evaluated, and the results were shown in FIG. 1A and FIG. 1B, respectively. As shown in FIG. 1A, compared with the positive control group (Amp H$_2$O), after being induced with anxiety by antibiotics and tube fed with the low-dose probiotic composition of the present invention (Amp/LABL), the nesting capacity of the mice was significantly improved on the twelfth day; and compared with the positive control group (Amp H$_2$O), after being induced with anxiety by antibiotics and tube fed with the high-dose probiotic composition of the present invention (Amp/LABH), the nesting capacity of the mice was significantly improved both on the eighth and twelfth day. The results indicate that the high-dose probiotic composition of the present invention can achieve efficacy in a relatively short period of time.

As shown in FIG. 1B, compared with the positive control group (Amp H$_2$O), after being induced with anxiety by antibiotics and tube fed with the low-dose probiotic composition of the present invention (Amp/LABL), the swimming survival ability of the mice was significantly improved on the eighth day; and compared with the positive control group (Amp H$_2$O), after being induced with anxiety by antibiotics and tube fed with the high-dose probiotic composition of the present invention (Amp/LABH), the swimming survival ability of the mice was also significantly improved on the eighth day.

According to the above results, after being induced with anxiety by antibiotics, no matter being fed with the low-dose or high-dose probiotic composition of the present invention, both of the nesting capacity and the swimming survival ability of the mice were significantly improved, indicating that both the low-dose and high-dose probiotic composition of the present invention can effectively improve anxious behavior of individuals caused by antibiotics, and the high-dose probiotic composition can achieve the effect more quickly in a short period of time.

In the embodiment of the present invention, in order to further compare and evaluate the efficacy of the probiotic composition of the present invention of a composite formula for improving anxious behavior with a single probiotic bacteria, the formula (I) of Example 1 was also used to quantify the efficacy of the swimming survival ability of the mice after being fed with the low-dose and high-dose probiotic composition, and the following formulas (II) was used to quantify the efficacy of the nesting capacity of the mice after being fed with the low-dose and high-dose probiotic composition:

$$\frac{\text{The difference in time the weight of cotton used for nesting(Test − sham)}}{\text{The difference in time the weight of cotton used for nesting(Control − sham)}} \times 100\%. \quad \text{(II)}$$

The quantified results were shown in Table 2. As shown in Table 2, after being fed with the low-dose probiotic composition of the group (13) or the high-dose probiotic composition of the group (14), the improvement of both the nesting capacity and the swimming survival ability of the mice was significantly better than that being fed with each of the *Lactobacillus rhamnosus* GM-020 of the group (1), the *Lactobacillus plantarum* GMNL-141 of the group (4), and the *Lactobacillus acidophilus* GMNL-185 of the group (5) in Example 1 alone.

whether the probiotic composition of the present invention achieves the efficacy of improving anxiety by adjusting the intestinal flora of individual.

In Example 2, after experimental animals were fed with the low-dose or high-dose probiotic composition of the present invention, the intestinal tissue of each mouse in the negative control group, the positive control group, and each experimental group was sampled. The distal ileum close to the cecum of each mouse was cut out, and the tissue was cut into pieces, and then the specimens were shaken with a homogenizer to homogenize the sampled intestinal tissue, and then centrifuged and the supernatant containing the intestinal flora microorganisms was obtained. The QIAamp rapid DNA isolation kit (Qiagen, Germany) was used for DNA extraction of the intestinal flora microorganisms according to the standard operation manual. Then, micro-volume Spectrometer (NanoDrop 2000) was used to detect the concentration of the extracted DNA (the ratio of OD 260 to OD 280 must be between 1.7 and 2.2, and the DNA concentration must be greater than 50 ng/μL), and the elution buffer (EB) comprised in the kit was used to dilute each sample to 4-6 ng/μL for subsequent sequencing analysis of 16S rRNA (16S ribosomal RNA) for identifying the species composition of the intestinal flora of each group of mice.

When performing the next-generation sequencing analysis of 16S IRNA, KAPA HiFi DNA polymerase (Roche, USA) was used to amplify the variable regions 3 and 4 of 16S rRNA (V3-V4), and the amplified DNA was purified with KAPA purification magnetic beads (Roche, USA). After the purified DNA was further purified by capillary electrophoresis (Fragment Analyzer, Advanced analytical, USA) and the quality thereof was confirmed by fluorescence spectrometer (Qubit 3.0, ThermoFisher, USA), the purified DNA was subjected to the second PCR to establish a library (Nextera XT Index Kit A, Illumina, USA), and the obtained PCR product was purified again with KAPA purification magnetic beads, and capillary electrophoresis and fluorescence spectrometer were used to confirm the quality and the concentration. When the concentration of the library-labeled DNA reached 4 nM, the purified DNA was mixed with 20% viral DNA (PhiX Control, Illumina, USA), and then, the

TABLE 2

| Group | Bacterial strains | n | Recovery rate of swimming survival ability (%, Mean ± SEM) | Recovery rate of nesting capacity (%, Mean ± SEM) |
|---|---|---|---|---|
| 13 | L. rhamnosus + L. plantarum + L. acidophilus | 5 | 171.4 ± 71.8 | 207.7 ± 59.9 |
| 14 | L. rhamnosus + L. plantarum + L. acidophilus | 5 | 234.3 ± 64.4 | 282.0 ± 29.6 |

Example 3

Improving Intestinal Flora with the Probiotic Composition for Improving Anxiety Caused by Antibiotics In the embodiment of the present invention, in order to further understand the mechanism of the probiotic composition of the present invention improving anxiety caused by antibiotics, the high-throughput next-generation sequencing (NGS) technology and bioinformatics were used to further analyze changes in intestinal flora of mice of which anxious behavior has been improved after being fed with the probiotic composition of the present invention, so as to evaluate MiSeq v3 600 cycle analysis kit was used for the next-generation sequencing of 16S rRNA of the intestinal flora of each group of mice.

Then, the results of the next-generation sequencing of the obtained 16S rRNA were analyzed by bioinformatics. First, the Fastq obtained from the next-generation sequencing was analyzed by Qiime2 analysis software to remove DNA fragments less than 400 with DaDa2, and compare the 97% similar sequence fragments in the Greengene v13.8 database to establish Operational Taxonomic Unit (OTU) table; wherein, the bacteria in the intestinal flora of each group of mice were classified by with bacterial phylum OUTs and bacterial genus OUTs, and the analysis results were shown as histograms of FIGS. 2A and 2B, respectively. Each column was the average change of the intestinal flora of multiple mice.

Figure 2A:
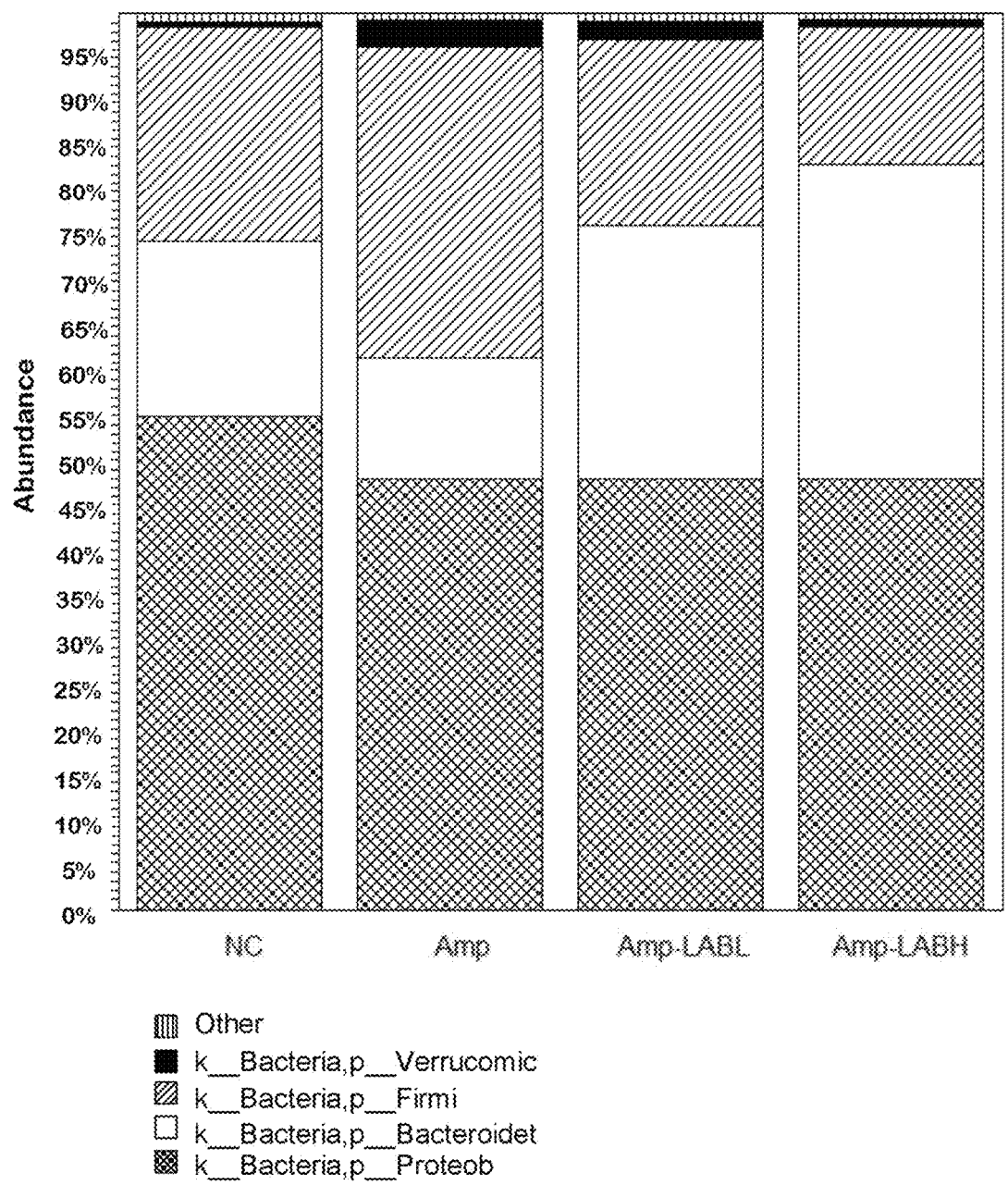
FIG. 2A shows the operational taxonomic unit (OTU) table of intestinal flora in mice after being fed with the probiotic composition of the present invention by classifying with phylum.
Figure 2B:
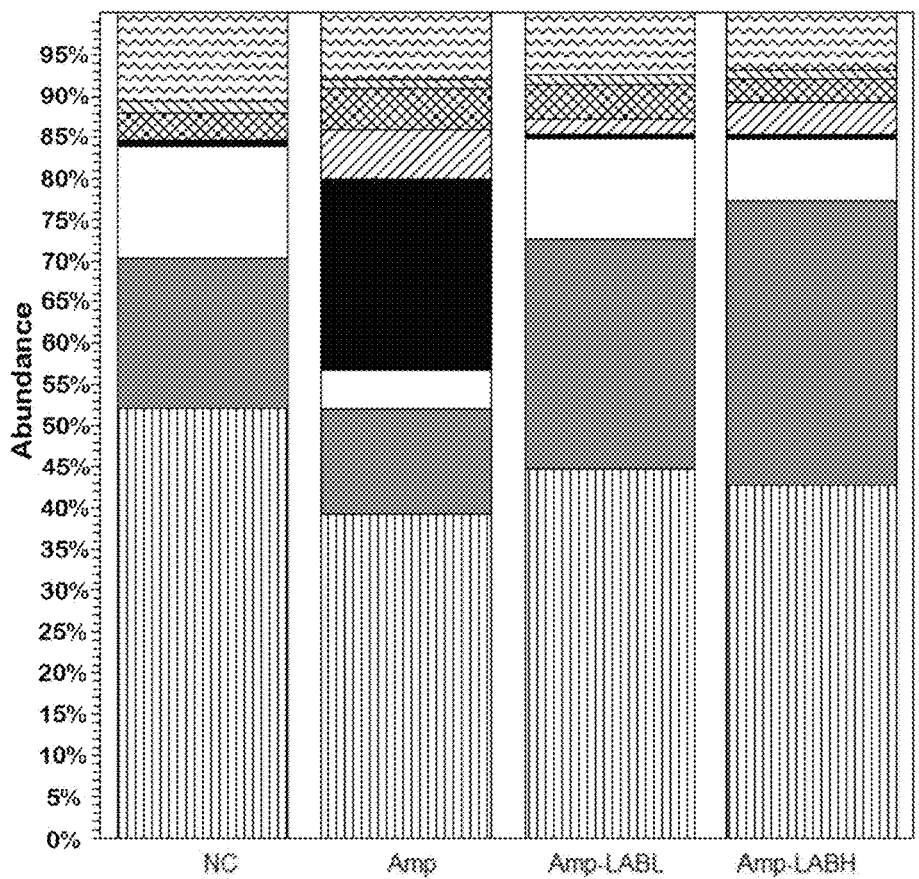
FIG. 2B shows the operational taxonomic unit (OTU) table of intestinal flora in mice after being fed with the probiotic composition of the present invention by classifying with genus.

As shown is FIGS. 2A and 2B, compared with the negative control group in which the mice have not been fed with antibiotics, the intestinal flora of the mice was significantly changed after being fed with antibiotics; after being induced with anxiety by antibiotics and then tube fed with the low-dose or high-dose probiotic composition of the present invention, the intestinal flora of the mice grew into intestinal flora of healthy mice that were more similar to the negative control group. More specifically, in the intestinal flora of the mice from the positive control group (Amp) fed with antibiotics, the abundance of *Firmicutes* and *Staphylococcus* was significantly increased, while the abundance of *Bacteroidetes, Lactobacillus*, and *Bacteroidales* (f_S24-7) was significantly decreased; however, in the intestinal flora of the mice from the negative control group, the experimental group in which the mice were fed with the low-dose probiotic composition of the present invention, and the experimental group in which the mice were fed with the high-dose probiotic composition of the present invention showed a completely opposite distribution trend. The results indicate that the probiotic composition of the present invention can restore the alteration and imbalance of intestinal flora caused by antibiotics to a healthy intestinal flora.

Example 4

The Probiotic Composition Increases the Abundance of Intestinal Species of Individuals with Anxiety Caused by Antibiotics Studies have shown that taking antibiotics may reduce the alpha diversity of the intestinal flora; therefore, in the embodiments of the present invention, in order to further evaluate whether the probiotic composition of the present invention can improve the decrease in the alpha diversity caused by antibiotics, the intestinal flora of mice of which anxious behavior has been improved after being fed with the probiotic composition of the present invention was further analyzed; wherein, alpha diversity refers to the biodiversity of a single cluster within a sample or habitat. The specific analysis method was to directly perform species diversity analysis (alpha Diversity, Shannon Diversity) on the aforementioned operational taxonomic unit obtained by the Qiime2 analysis software, and the results were shown as FIG. 3.

Figure 3:
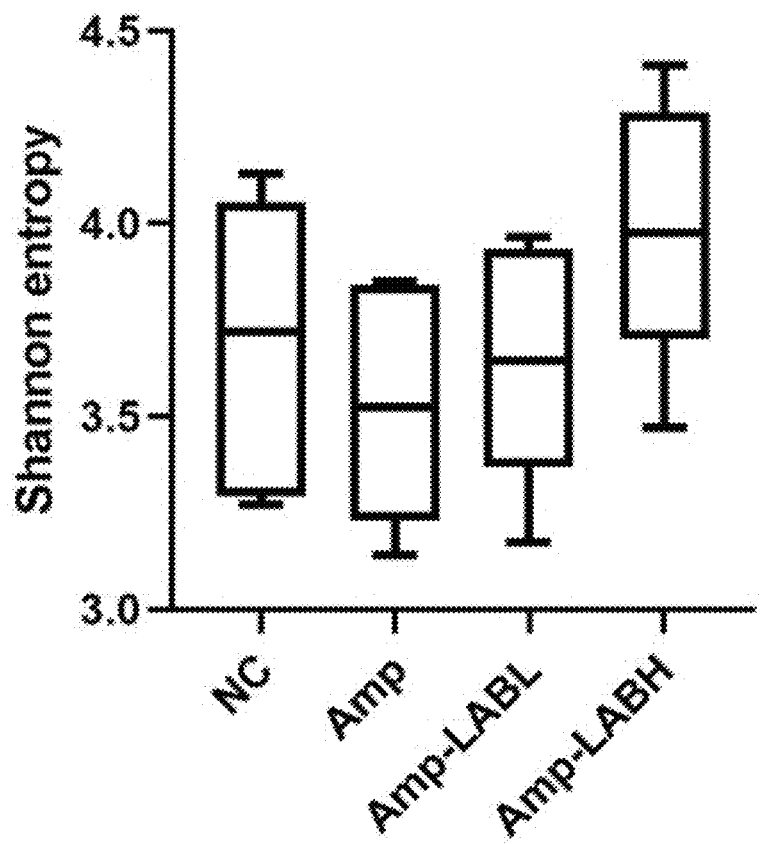
FIG. 3 shows the results of alpha diversity of intestinal flora in mice after being fed with the probiotic composition of the present invention.

As shown in FIG. 3, compared with the negative control group in which the mice have not been fed with antibiotics, the diversity of intestinal flora of the mice was indeed decreased after being fed with antibiotics; after being induced with anxiety by antibiotics and then tube fed with the low-dose or high-dose probiotic composition of the present invention, the diversity of intestinal flora of the mice could be restored quickly. The result indicates that the probiotic composition of the present invention can help stabilize the bacterial flora of individuals and restore the health of the intestinal tract quickly.

In addition, when studying the diversity of flora in individuals, clade diagrams are often used to present the analysis results of the next-generation sequencing of 16S rRNA, and LEfSe analysis (Linear discriminant analysis, LDA, Effect Size) is mostly used to calculate the clade diagrams; LEfSe analysis is an analysis algorithm for finding high-dimensional biomarkers and screening genomic features, and can find biomarkers with statistically significant differences between groups. When applied to microbial diversity analysis, LEfSe analysis can find out the microbial species with significant differences in abundance between groups, and such algorithm emphasizes statistical significance and biological relevance. Therefore, in the embodiment of the present invention, LEfSe analysis online software provided by Galaxy—The Huttenhower Lab was further used to analyze the main microorganisms within the intestinal flora of each group of mice, and a significant core flora was determined when the LDA Score was greater than 2, and the analysis results were shown in FIG. 4.

Figure 4:
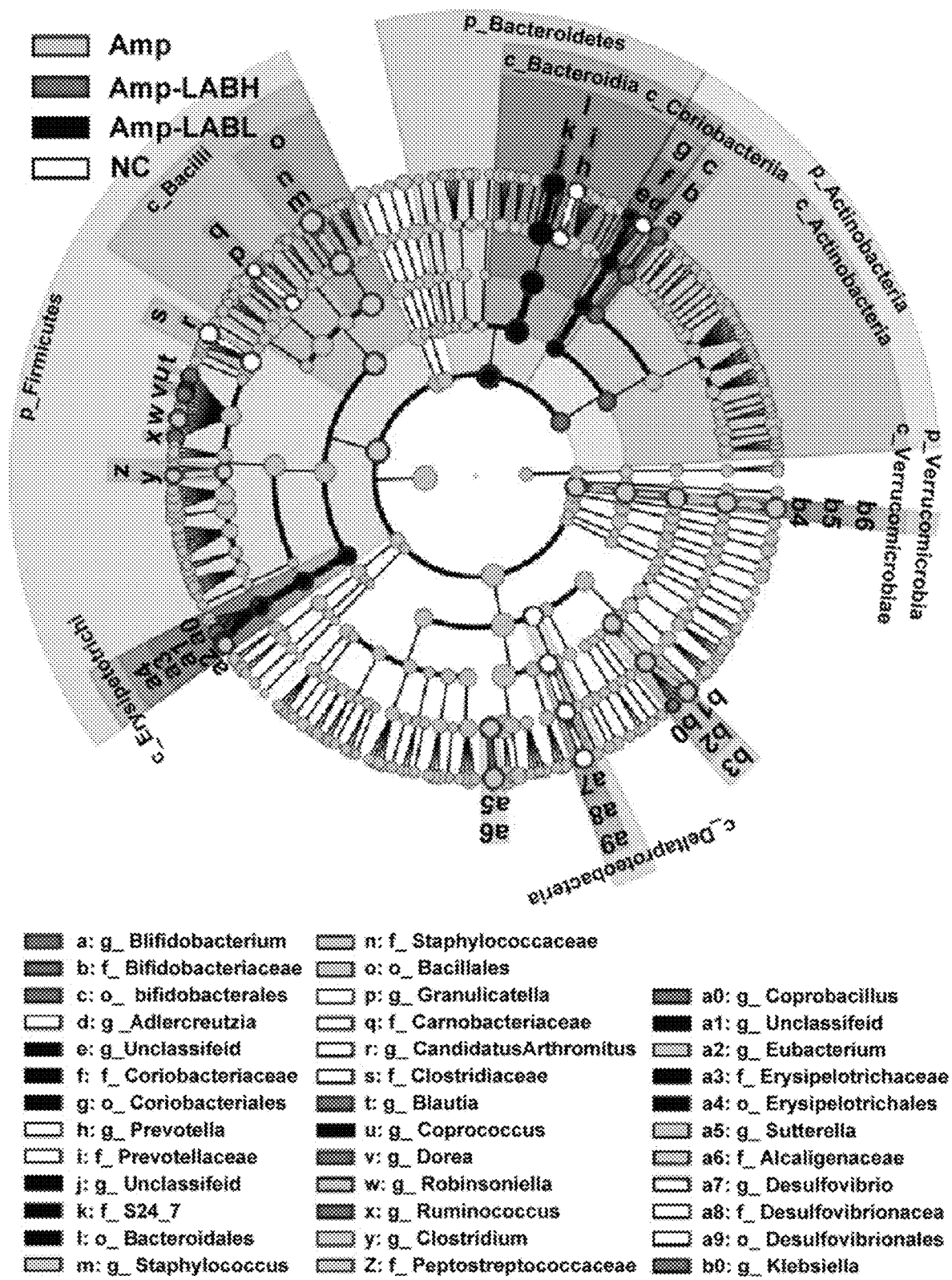
FIG. 4 shows the results of LEfSe analysis of intestinal flora in mice after being fed with the probiotic composition of the present invention, and the negative and the positive control groups.
Figure 5A:
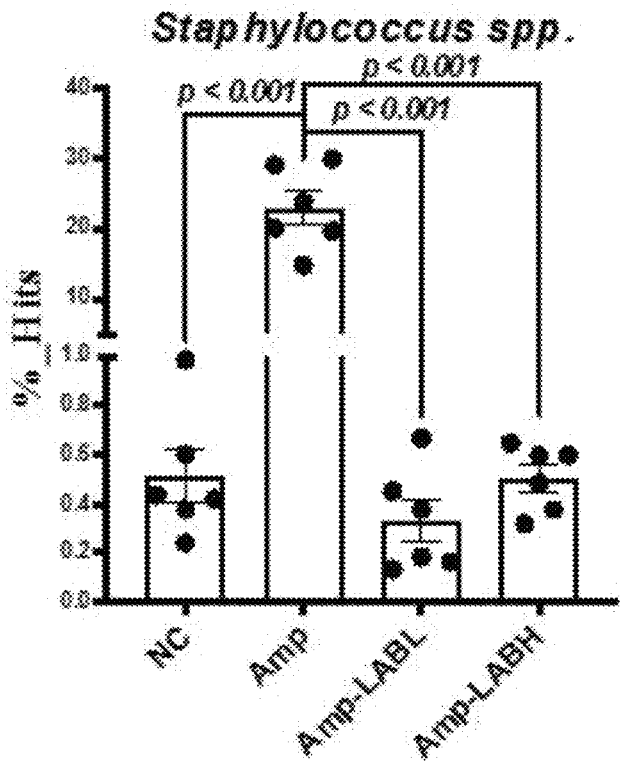
FIG. 5A shows the abundance of *Staphylococcus* in intestinal flora of mice according to the results of LEfSe analysis in FIG. 4; wherein, Hits represents the frequency which the instrument has detected to the *Staphylococcus*.
Figure 5B:
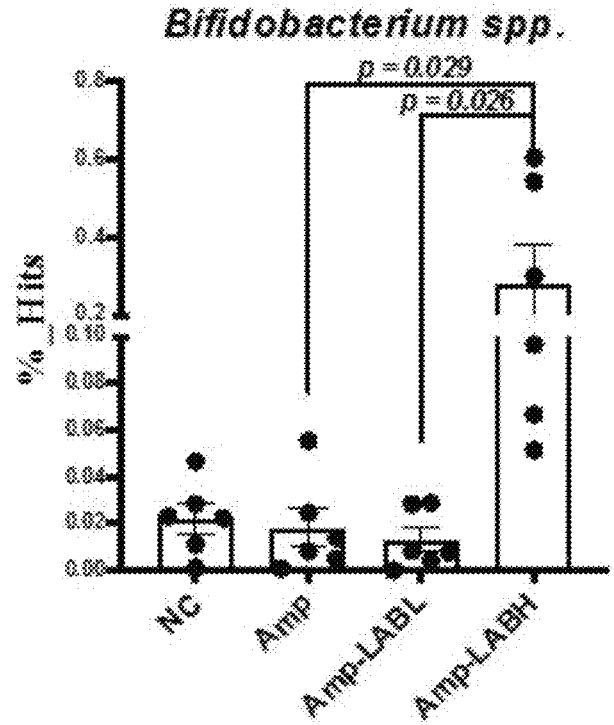
FIG. 5B shows the abundance of *Bifidobacterium* in intestinal flora of mice according to the results of LEfSe analysis in FIG. 4; wherein, Hits represents the frequency which the instrument has detected to the *Bifidobacterium*.

In the clade diagrams of FIG. 4, the circles radiating from the inside to the outside represent the taxonomic hierarchy from the phylum to the genus (or species), and each small circle in a different classification level represents a taxonomic group at that level, and the diameter of these small circles represents relative abundance thereof. Then, the types of microorganisms that have significant differences between the groups were colored according to the representative colors of their original groups (i.e. the negative control group, the positive control group, the experimental group in which the mice were fed with the low-dose probiotic composition of the present invention, and the experimental group in which the mice were fed with the high-dose probiotic composition of the present invention), and then the bacterial family, genus, and species with significant changes in intestinal flora of each group of mice were listed in Table 3. The abundances of *Staphylococcus* and *Bifidobacterium*, which showed the most significant differences, in each group were plotted as shown in FIG. 5A and FIG. 5B; wherein, during bacterial flora analysis, the number of times a bacterium was detected by the instrument was represented by Hits, and therefore, the higher the number of hits or the higher the proportion of hits, the greater the total number of detected bacteria.

TABLE 3

| Group | Classification | | |
|---|---|---|---|
| | Order | Family | Genus |
| NC | Desulfovibrionales | Prevotellaceae | *Adlercreutzia* |
| | | Carnobacteriaceae | *Prevotella* |
| | | Clostridiaceae | *Granulicatella* |
| | | Desulfovibrionaceae | *CandidatusArthromitus* |
| | | | *Desulfovibrio* |
| Amp | Bacillales | Staphylococcaceae | *Staphylococcus* |
| | | Peptostreptococcaceae | *Robinsoniella* |
| | | Alcaligenaceae | *Clostridium* |
| | | | *Eubacterium* |
| | | | *Sutterella* |

TABLE 3-continued

| Group | Order | Family | Genus |
|---|---|---|---|
| Amp-LABL | Coriobacteriales | Coriobacteriaceae | Unclassifeid |
| | Bacteroidales | S24_7 | *Coprococcus* |
| | Erysipelotrichales | Erysipelotrichaceae | |
| Amp-LABH | Bifidobacteriales | Bifidobacteriaceae | *Bifidobacterium* |
| | | | *Blautia* |
| | | | *Dorea* |
| | | | *Ruminococcus* |
| | | | *Coprobacillus* |
| | | | *Klebsiella* |

As shown in FIG. 5A and FIG. 5B, compared with the intestinal flora of the other three groups, in the intestinal flora of the mice from the positive control group which were induced with anxiety by being fed with antibiotics, the abundance of *Staphylococcus* was significantly increased, indicating that *Staphylococcus* is related to the appearance of individual anxious behavior; in addition, after being induced with anxiety by antibiotics and then tube fed with the low-dose or high-dose probiotic composition of the present invention, the abundance of *Bifidobacterium* in the intestinal flora of mice was significantly increased, indicating that *Bifidobacterium* is related to the mechanism of the probiotic composition of the present invention to improve anxious behavior of individuals caused by antibiotics, and Bacteria from *Bifidobacterium* are beneficial to human health and have a positive effect on emotional stability.

According to the above analysis results, the probiotic composition of the present invention can improve imbalance of the intestinal microbiota caused by antibiotics, help restore and stabilize diversity of the intestinal flora species, and increase the abundance of *Bifidobacterium* spp. to improve anxiety caused by antibiotics.

Example 5

The Probiotic Composition Increases the Synthesis of Emotionally Stabilizing Substances of Individuals with Anxiety Caused by Antibiotics In the embodiment of the present invention, in order to understand the intestinal microbes regulated by the probiotic composition of the present invention, Phylogenetic Investigation of Communities by Reconstruction of Unobserved States 2 (PICRUSt2) was further used to analyze pathways involved in the intestinal microbes of the aforementioned groups of mice to understand which biological pathways the probiotic composition of the present invention affects individuals for improving anxious behavior caused by antibiotics; wherein, PICRUSt2 is a set of tools to predict the functional abundance of microorganisms based on the sequence of the marked gene, and can be applied to predict the function of the 16S rRNA sequence.

First, the 16S rRNA sequencing results of the intestinal flora of each group of mice obtained in Example 3, including the negative control group, the experimental group in which the mice were fed with the low-dose probiotic composition of the present invention, and the experimental group in which the mice were fed with the high-dose probiotic composition of the present invention, were used to predict and analyze the biological pathways that intestinal microbes involved in through PICRUSt2. Then, the biological pathways obtained from the prediction and analysis of each group were divided into the following groups: (1) the negative control group (NC) compared with the positive control group (Amp); (2) the positive control group (Amp) compared with the experimental group in which the mice were fed with the low-dose probiotic composition of the present invention (Amp-LABL); and (3) the positive control group (Amp) the experimental group in which the mice were fed with the high-dose probiotic composition of the present invention (Amp-LABH), and each two of them were compared to find out the statistically different biological pathways; wherein, all analysis results were considered statistically significant when the p value was less than 0.05.

Figure 6:
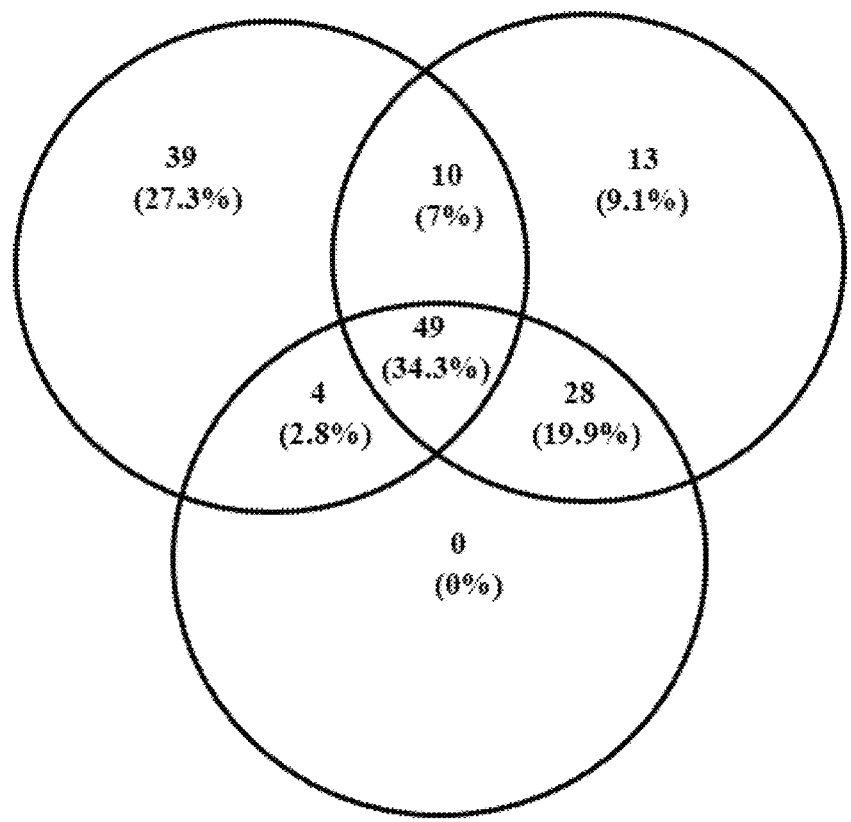
FIG. 6 shows a schematic diagram of the intersection of the physiological regulation pathways with statistically differences in each group after PICRUSt2 analysis using the Venn diagram.

Then, the Venn diagram was used to intersect the biological pathways that were with statistical differences found in the aforementioned three comparisons to further find out the bio-pathways that were with statistical differences in all of these three comparisons, and the results were shown as FIG. 6. As shown in FIG. 6, in the comparison of the negative control group (NC) compared with the positive control group (Amp), the differences of intestinal flora in mice affected about 102 biological pathways; in the comparison of the positive control group (Amp) compared with the experimental group in which the mice were fed with the low-dose probiotic composition of the present invention (Amp-LABL), the differences of intestinal flora in mice affected about 100 biological pathways; and in the comparison of the positive control group (Amp) compared with the experimental group in which the mice were fed with the high-dose probiotic composition of the present invention (Amp-LABH), the differences of intestinal flora in mice affected about 81 biological pathways; wherein, the 49 biological pathways were the common pathways with statistical differences in all of these three comparisons.

In order to understand the biological pathways related to the improvement of anxious behavior caused by antibiotics with the probiotic composition of the present invention, the specific 49 biological pathways that showed an increasing (I) or decreasing (D) trend in each of these three comparisons were listed in Table 4. As shown in Table 4, the biosynthesis of flavone and flavonol, the biosynthesis of isoquinoline alkaloid, and the metabolism of nicotinate and nicotinamide (i.e. the metabolism of vitamin B3 in the form of amide) showed a decreasing trend in the group in which the mice were induced with anxiety by being fed with antibiotics; however, in the group in which the mice were induced with anxiety and then fed with the low-dose or high-dose probiotic composition of the present invention, these three pathways showed an increasing trend. Also, previous studies have shown that the substances synthesized by these three biological pathways are all substances that can increase emotional stability and improve individual anxiety. The results indicate that the probiotic composition of the present invention can restore the biological pathways that are decreased due to antibiotics to increase the synthesis of emotionally stabilizing substances, and are beneficial for improving anxiety caused by antibiotics.

TABLE 4

| Pathway | Amp vs. NC | Amp-LABL vs. Amp | Amp-LABH vs. Amp |
|---|---|---|---|
| Amoebiasis | I | D | D |
| Arginine and proline metabolism | D | I | I |
| Atrazine degradation | I | D | D |
| Bacterial toxins | D | I | I |
| Biosynthesis of siderophore group nonribosomal peptides | I | D | D |
| Biosynthesis of vancomycin group antibiotics | D | I | I |
| Cellular antigens | D | I | I |
| Chromosome | D | I | I |
| Cyanoamino acid metabolism | D | I | I |
| Cytoskeleton proteins | D | I | I |
| D-Alanine metabolism | I | D | D |
| D-Arginine and D-ornithine metabolism | I | D | D |
| Energy metabolism | D | I | I |
| Fatty acid biosynthesis | I | D | D |
| Flavone and flavonol biosynthesis | D | I | I |
| Glycerolipid metabolism | I | D | D |
| Glycerophospholipid metabolism | I | D | D |
| Isoquinoline alkaloid biosynthesis | D | I | I |
| Linoleic acid metabolism | I | D | D |
| Meiosis - yeast | I | D | D |
| Membrane and intracellular structural molecules | D | I | I |
| Metabolism of cofactors and vitamins | I | D | D |
| Nicotinate and nicotinamide metabolism | D | I | I |
| Nitrogen metabolism | I | D | D |
| Other ion-coupled transporters | I | D | D |
| Penicillin and cephalosporin biosynthesis | D | I | I |
| Phosphonate and phosphinate metabolism | I | D | D |
| Phosphotransferase system (PTS) | I | D | D |
| Plant-pathogen interaction | D | I | I |
| Polyketide sugar unit biosynthesis | D | I | I |
| Pores ion channels | D | I | I |
| Primary immunodeficiency | D | I | I |
| Protein folding and associated processing | I | D | D |
| Protein processing in endoplasmic reticulum | D | I | I |
| Proximal tubule bicarbonate reclamation | D | I | I |
| Pyruvate metabolism | I | D | D |
| Renal cell carcinoma | I | D | D |
| Riboflavin metabolism | I | D | D |
| Shigellosis | I | D | D |
| Signal transduction mechanisms | I | D | D |
| Staphylococcus aureus infection | I | D | D |
| Streptomycin biosynthesis | D | I | I |
| Sulfur metabolism | I | D | D |
| Sulfur relay system | I | D | D |
| Taurine and hypotaurine metabolism | D | I | I |
| Tetracycline biosynthesis | I | D | D |
| Ubiquitin system | I | D | D |
| alpha-Linolenic acid metabolism | I | D | D |
| beta-Lactam resistance | D | I | I |

In addition, as shown in Table 4, *Staphylococcus aureus* infection showed an increasing trend in the group in which the mice were induced with anxiety by being fed with antibiotics, while in the group in which the mice were induced with anxiety and then fed with the low-dose or high-dose probiotic composition of the present invention *Staphylococcus aureus* infection showed a decreasing trend. Previous studies showed that *Staphylococcus aureus* infection would cause disorders in individual's bacterial flora and affect the production and synthesis of short-chain fatty acids (SCFAs). The results indicate that the probiotic composition of the present can alleviate the increase in *Staphylococcus aureus* infections caused by antibiotics to provide a beneficial effect on improving anxious behavior of individuals caused by antibiotics.

Example 6

The Probiotic Composition Increases the Synthesis of SCFA in Individuals with Anxiety Caused by Antibiotics Since previous studies showed that short-chain fatty acids secreted by individual intestinal microbes help stabilize the individual's emotion, cognition, and behavior to effectively reduce the occurrence of anxiety, in the embodiment of the present invention, the ability of the probiotic composition of the present invention for enhancing the synthesis of short-chain fatty acids in intestinal tract of individual was further tested to provide efficacy of improving individual anxious caused by antibiotics.

As described in Example 2, after being fed with the low-dose or high-dose probiotic composition of the present invention, the feces of each group of mice, including the negative control group, the experimental group in which the mice were fed with the low-dose probiotic composition of the present invention, and the experimental group in which the mice were fed with the high-dose probiotic composition of the present invention, were respectively sampled. The feces from different mice in the same group were mixed into a single tube for following analysis. Then, Gas Chromatography Mass Spectrometry (GC/MS) was used to analyze the components of short-chain fatty acids in the feces of each analysis sample, and the results showed in units of μmol/g; wherein, the short-chain fatty acids mainly includes acetic acid, propionic acid, and butyric acid.

The detailed sample processing and detection methods were briefly described as followings: first, 0.5 g of feces from each analysis sample was taken and placed in a 15 mL centrifuge tube, and then 5 mL of pure water was added to dissolve the samples, and then each centrifuge tube was vortexed for 2 minutes; after centrifugation (7000 rpm, 5 minutes), the supernatant was collected, filtered (0.45 μm), and then was put into a new 15 mL centrifuge tube as the GC/MS analysis sample of each test group; then, 2 mL of the GC/MS analysis sample was taken into a new 15 mL centrifuge tube, and 0.2 mL of 50% sulfuric acid solution was added, and 2 mL of ether was then added, and the solution was inverted for 30 times before centrifugation (>10,000 rpm, 5 minutes); the solution was then placed in the refrigerator (4° C.) for 30 minutes, then the upper ether solution layer was collected and analyzed with a gas chromatography mass spectrometer (GC/MS). The conditions of gas mass spectrometry were as followings: FFAP elastic quartz capillary column (30 m×0.25 mm×0.25 μm) was used; column temperature program was: 100° C. (1 minute), 5° C./minute to 150° C. (5 minutes); carrier gas was: high pure nitrogen, purity ≥99.999%; carrier gas flow rate was 2 mL/min; injection port temperature was 270° C.; sampling method was: splitless injection, injection volume 2.0 μL; detector temperature (FID) was 280° C. Finally, the standard product was used as the comparison baseline to convert the content of six types of short-chain fatty acids per gram of each analysis sample, and the units was μmole/g.

The analysis results of the short-chain fatty acid lipid content in the feces of each group of mice were shown in Table 5. As shown in Table 5, compared with the negative control group in which the mice have not been fed with antibiotics, the content of acetic acid in the feces of mice would be slightly decreased while the content of propionic acid and butyric acid would be significantly decreased after being induced with anxiety by antibiotics. After being induced with anxiety by antibiotics and then tube fed with the low-dose or high-dose probiotic composition of the present invention, all the content of acetic acid, propionic acid, and butyric acid in the feces of mice would be significantly increased. The results indicate that the decrease of short-chain fatty acids in individual's intestinal tract would indeed lead to anxious behavior, and the probiotic composition of the present invention can improve the individual's anxiety caused by antibiotics through increasing the synthesis of short-chain fatty acids in the individual's intestinal tract.

TABLE 5

| SCFA | Group | | | |
| --- | --- | --- | --- | --- |
| | NC | Amp | Amp-LABL | Amp-LABH |
| Acetic acid (umole/g stool) | 7.77 | 6.43 | 12.10 | 8.02 |
| Propionic acid (umole/g stool) | 2.47 | 0.90 | 4.18 | 3.02 |
| Butyric acid (umole/g stool) | 5.87 | 0.75 | 1.64 | 2.29 |

In summary, according to the present invention, the *Lactobacillus rhamnosus* GM-020, the *Lactobacillus plantarum* GMNL-141, and the *Lactobacillus acidophilus* GMNL-185 that provide the best efficacy in improving anxiety caused by antibiotics are screened out by animal experiments, and these three probiotic bacteria are prepared into the probiotic composition of the present invention in a compound formula. Moreover, no matter the low-dose or high-dose probiotic composition of the present invention is proved to effectively improve the anxious behavior of individuals caused by antibiotics, and the efficacy thereof is better than that of a single probiotic bacteria.

Furthermore, the probiotic composition of the present invention can improve the imbalance of individual intestinal flora caused by antibiotics, and assist in stabilizing and increasing the intestinal flora species richness, especially increasing the abundance of *Bifidobacterium* and decreasing the abundance of *Staphylococcus*, so that the individual intestinal flora can quickly return to a state close to that of a healthy individual. In addition, the probiotic composition of the present invention can increase the biosynthesis of flavonoids and flavonols, the biosynthesis of isoquinoline alkaloids, and nicotinate, and the metabolism of nicotinate and nicotinamide by adjusting the intestinal flora of individuals, and can also directly increase the synthesis of short-chain fatty acids in intestine, thereby improving individual anxiety or anxious behavior caused by antibiotics.

What is claimed is:

1. A method of improving anxiety caused by an antibiotic, comprising:
administering to a subject in need thereof a *Lactobacillus* composition, wherein the *Lactobacillus* composition consists of a *Lactobacillus plantarum* GMNL-141, a *Lactobacillus rhamnosus* GM-020, and a *Lactobacillus acidophilus* GMNL-185, wherein the *Lactobacillus plantarum* GMNL-141 is deposited at National Institute of Technology and Evaluation (NITE) with an accession number NITE BP-03510, wherein the *Lactobacillus plantarum* GMNL-141 is in a lyophilized or spray dried form, wherein the *Lactobacillus rhamnosus* GM-020 is deposited at China Type Culture Collection (CCTCC) with an accession number CCTCC M203098, wherein the *Lactobacillus acidophilus* GMNL-185 is deposited at CCTCC with an accession number CCTCC M2017764;
wherein the *Lactobacillus plantarum* GMNL-141, the *Lactobacillus rhamnosus* GM-020, and the *Lactobacillus acidophilus* GMNL-185 are mixed with a ratio of 1:1:1.

2. The method according to claim 1, wherein the antibiotic is Ampicillin.

3. The method according to claim 1, wherein the *Lactobacillus* composition improves imbalance of intestinal flora and/or decrease in intestinal flora species richness caused by the antibiotic.

4. The method according to claim 1, wherein the *Lactobacillus* composition increases abundance of *Bifidobacterium* and/or decreases abundance of *Staphylococcus* in intestinal flora.

5. The method according to claim 1, wherein the *Lactobacillus* composition increases synthesis of flavone and flavonol, synthesis of isoquinoline alkaloid, and/or synthesis of nicotinate and nicotinamide.

6. The method according to claim 1, wherein the *Lactobacillus* composition increases synthesis of short-chain fatty acids (SCFAs) in intestine.

* * * * *

SEQUENCE LISTING

```
<160> NUMBER OF SEQ ID NOS: 3

<210> SEQ ID NO 1
<211> LENGTH: 20
<212> TYPE: DNA
<213> ORGANISM: Artificial sequence
<220> FEATURE:
<223> OTHER INFORMATION: PCR primer

<400> SEQUENCE: 1
agagtttgat cctggctcag                                                20
```

```
<210> SEQ ID NO 2
<211> LENGTH: 18
<212> TYPE: DNA
<213> ORGANISM: Artificial sequence
<220> FEATURE:
<223> OTHER INFORMATION: PCR primer

<400> SEQUENCE: 2
gtattaccgc ggctgctg                                                 18

<210> SEQ ID NO 3
<211> LENGTH: 527
<212> TYPE: DNA
<213> ORGANISM: Lactobacillus plantarum

<400> SEQUENCE: 3
ggcgtgcggc gtgctataca tgcaagtcga acgaactctg gtattgattg gtgcttgcat    60
catgatttac atttgagtga gtggcgaact ggtgagtaac acgtgggaaa cctgcccaga   120
agcgggggat aacacctgga aacagatgct aataccgcat aacaacttgg accgcatggt   180
ccgagtttga aagatggctt cggctatcac ttttggatgg tcccgcggcg tattagctag   240
atggtggggt aacggctcac catggcaatg atacgtagcc gacctgagag ggtaatcggc   300
cacattggga ctgagacacg gcccaaactc ctacgggagg cagcagtagg gaatcttcca   360
caatggacga aagtctgatg gagcaacgcc gcgtgagtga agaagggttt cggctcgtaa   420
aactctgttg ttaaagaaga acatatctga gagtaactgt tcaggtattg acggtattta   480
accagaaagc cacggctaac tacgtgccag cagccggggt aatacaa                 527
```